US00PP21732P2

(12) United States Plant Patent
Khemakongkanond

(10) Patent No.: US PP21,732 P2
(45) Date of Patent: Feb. 22, 2011

(54) *DRACAENA* PLANT NAMED 'SUPHA06'
(50) Latin Name: *Dracaena reflexa*
Varietal Denomination: SUPHA06

(76) Inventor: Kanchana Khemakongkanond, 126 Pattanakan Lane 65 Off 5, Bangkok (TH) 10250

( * ) Notice: Subject to any disclaimer, the term of this patent is extended or adjusted under 35 U.S.C. 154(b) by 0 days.

(21) Appl. No.: 12/589,196

(22) Filed: Oct. 19, 2009

(51) Int. Cl.
*A01H 5/00* (2006.01)

(52) U.S. Cl. ..... Plt./383
(58) Field of Classification Search ..... Plt./383

See application file for complete search history.

*Primary Examiner*—Annette H Para

(57) ABSTRACT

A new and distinct *Dracaena reflexa* cultivar named 'SUPHA06' is disclosed, characterized by distinctive foliage variegation, not seen in other *Dracaena reflexa* cultivars. The new variety is a *Dracaena,* and is normally used as an ornamental plant.

1 Drawing Sheet

Figure 1:
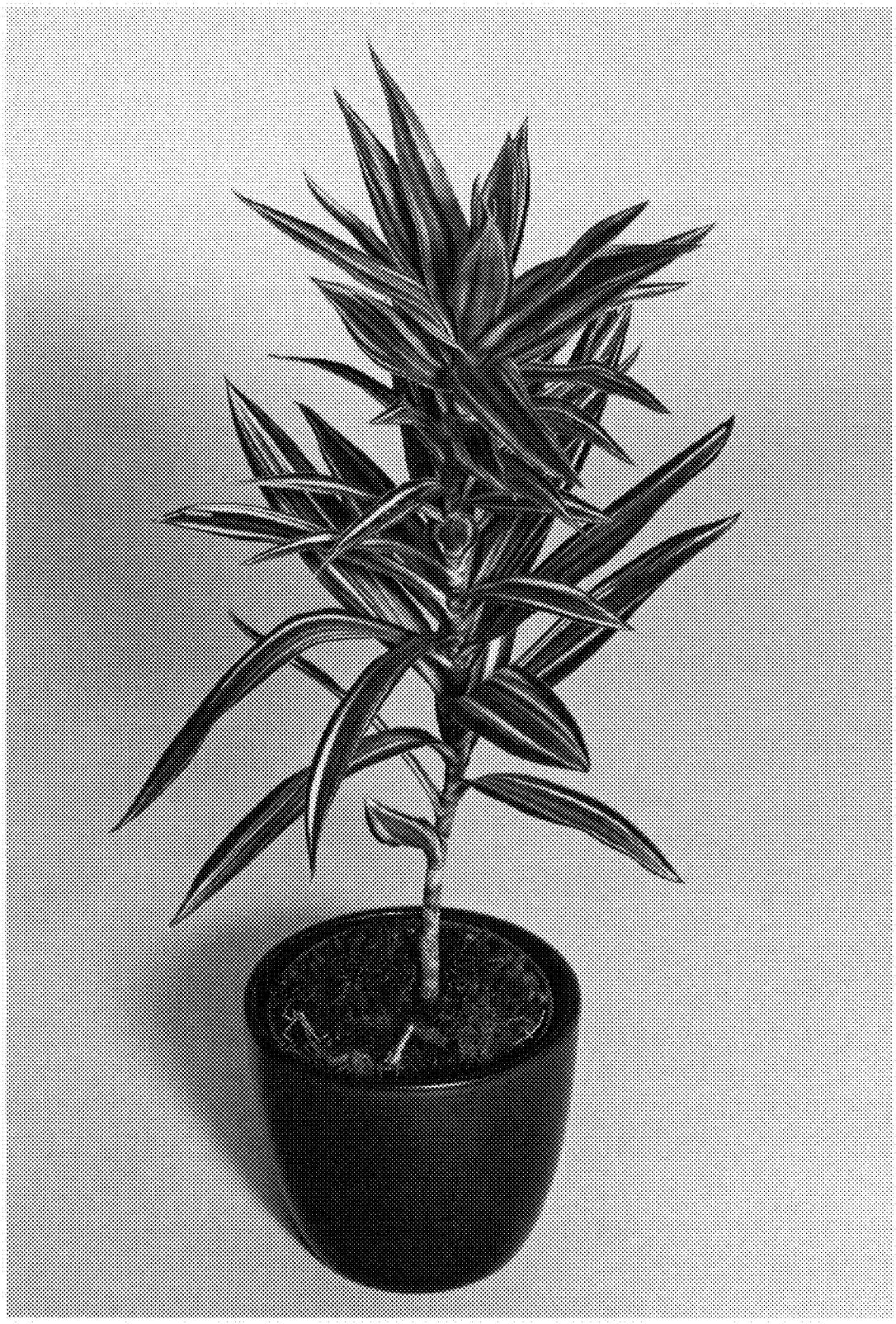

Latin name of the genus and species: *Dracaena reflexa.*
Variety denomination: 'SUPHA06'.

BACKGROUND OF THE INVENTION

The new cultivar was discovered as a chance, whole plant mutation in a commercial nursery in Chonburi, Thailand. The inventor, Kanchana Khemakongkanond, a citizen of Thailand, discovered the new variety as a naturally occurring whole plant mutation among several hundred plants of the unpatented commercial variety, *Dracaena reflexa* 'Song of Jamaica'. The new variety was discovered in August 2004 by the inventor.

Asexual reproduction of the new cultivar 'SUPHA06' by vegetative cuttings was performed at a commercial nursery in Chonburi, Thailand in April 2005. Since that time, many generations have been reproduced, and have shown that the unique features of this cultivar are stable and reproduced true to type through successive generations.

SUMMARY OF THE INVENTION

The cultivar 'SUPHA06' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SUPHA06.' These characteristics in combination distinguish 'SUPHA06' as a new and distinct *Dracaena reflexa* cultivar:

1. Distinctive foliage variegation pattern unlike other known *Dracaena reflexa* cultivars.

PARENT COMPARISON

Plants of the new cultivar 'SUPHA06' are similar to plants of the parent variety *Dracaena reflexa* 'Song of Jamaica' in most horticultural characteristics. However, plants of the new cultivar 'SUPHA06' produce foliage variegation containing yellow, whereas 'Song of Jamaica' has no yellow variegation. Also, specifically,

COMMERCIAL COMPARISON

In addition to the parent variety, 'Supha06' can also be compared to the unpatented, commercially known variety *Dracaena reflexa* 'Song of India'. The new variety produces foliage with a variety of colors, green, light green and yellow in fine lines and stripes along the leaf, and the leaf margin. 'Song of India' produces foliage with a wide green center and yellow margins only.

BRIEF DESCRIPTION OF THE PHOTOGRAPH

The accompanying photograph in FIG. 1 illustrates in full color a typical plant of 'SUPHA06' grown in a greenhouse. The pot size is a commercial 11.5 cm container. The plant shown is approximately 5 months old. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used. The following observations and measurements describe 'SUPHA06' plants grown in a commercial greenhouse in Honselersdijk, The Netherlands from early Winter to early Spring. The growing temperature ranged from approximately 20 to 21° C. at night and 20 to 22° C. during the day. Measurements and numerical values represent averages of typical flowering types. No chemical or photoperiodic treatments were given.

Botanical classification: *Dracaena reflexa* 'SUPHA06.'

PROPAGATION

Time to initiate rooting: About 5 weeks at approximately 25 to 26° C.

Root description: Moderately thick, moderately fibrous, not fleshy, young roots colored near RHS Yellow-White 158D older roots near RHS Greyed-Orange 163D..

PLANT

Age of plant described: Approximately 5 months.
Pot size of plant described: Approximately 11.5 cm.
Growth habit: Upright.
Height: Approximately 43.1 cm.
Plant spread: Approximately 26.7 cm.
Growth rate: Moderate. Approximately 8 cm per month.
Branching characteristics: Not free branching, growing with one main stem from the base. Will only develop lateral branches after pinching/pruning.
Diameter of stem: Approximately 0.7 cm.
Internode length: Average 0.6 cm.
Texture of stem: Smooth, dull.
Color of stem: Near RHS Grey-Brown 199B to 199D.
Stem strength: Very strong.
Number of leaves per stem: Average 43.

FOLIAGE

Leaf:

*Arrangement.*—Alternate, whorled.
*Average length.*—Approximately 12.2 cm.
*Average width.*—Approximately 2.3 cm.
*Shape of blade.*—Lorate.
*Aspect.*—Slightly curved downward.
*Apex.*—Acuminate.
*Base.*—Broad cuneate.
*Attachment.*—Sheathing.
*Margin.*—Entire.
*Texture of top surface.*—Smooth, moderately glossy.
*Texture of bottom surface.*—Smooth, moderately glossy.
*Color.*—Young foliage upper side: Near RHS Green 137A and Green N137A and Green N137B, irregularly striped with both Yellow-Green N144A and Yellow-Green N144B. Young foliage under side: Near RHS Green N137B and N137C, irregularly striped with Yellow-Green 144C. Mature foliage upper side: Near RHS Green N137A and Green 139A and 147A, all colors present. Irregularly striped with Yellow-Green 144A and 144B and Yellow-Green 154D. Mature foliage under side: Near RHS Green N137A and N137B and Greyed-Green 191A. Irregularly striped with Yellow-Green 150D and Yellow-Green 154D.
*Venation.*—Type: parallel. Color: Upperside: Color identical/indistinguishable from leaf blade. Underside: Color identical/indistinguishable from leaf blade.
*Sheath.*—Average Length: Approximately 0.4 cm. Average Width: Approximately 0.7 cm. Color: Near RHS Yellow-Green 147D. Texture: smooth, moderately glossy.

FLOWER

Flowering not observed to date.

OTHER CHARACTERISTICS

Disease resistance: Neither resistance nor susceptibility to diseases or pests normal to *Dracaena* have been observed in this variety.
Drought tolerance and temperature tolerance: Tender perennial, low temperature tolerance to a maximum low of approximately −5° C. Tolerates high temperature extremely well, to at least 40° C. Some drought tolerance. Plants can be allowed in dry soil for several days without damage.
Fruit/seed production: Fruits and seeds have not been observed.

What is claimed is:

1. A new and distinct cultivar of *Dracaena* plant named 'SUPHA06' as herein illustrated and described.

* * * * *